United States Patent [19]

Bourguignon et al.

[11] Patent Number: 5,735,841
[45] Date of Patent: Apr. 7, 1998

[54] NON-SPIKABLE CONNECTOR

[75] Inventors: Michel Bourguignon, Lasson, France; Ignacio Larrain, Traverenges, Switzerland

[73] Assignee: Nestec, Ltd., Vevey, Switzerland

[21] Appl. No.: 613,345

[22] Filed: Mar. 11, 1996

[30] Foreign Application Priority Data

Mar. 13, 1995 [FR] France ................... 95 02881

[51] Int. Cl.⁶ ..................... A61B 19/00; A61M 5/32
[52] U.S. Cl. ........................... 604/411; 604/412
[58] Field of Search ................... 604/410, 262, 604/408, 404, 411, 414, 415, 251, 405, 406, 283, 905

[56] References Cited

U.S. PATENT DOCUMENTS

| | | | |
|---|---|---|---|
| 4,332,333 | 6/1982 | Linsey | 604/905 |
| 4,335,770 | 6/1982 | Kulle et al. | 604/408 |
| 4,432,763 | 2/1984 | Manschot et al. | 604/410 |
| 4,611,643 | 9/1986 | Beebe et al. | 604/905 |
| 4,655,763 | 4/1987 | Malcolm et al. | 604/411 |
| 4,723,956 | 2/1988 | Schnell et al. | 604/408 |
| 4,787,890 | 11/1988 | Ufermann | 604/411 |
| 4,798,605 | 1/1989 | Steiner et al. | 604/411 |
| 4,826,500 | 5/1989 | Rautsola | 604/411 |
| 4,969,879 | 11/1990 | Lichte | 604/905 |
| 4,983,161 | 1/1991 | Dadson et al. | 604/905 |
| 5,137,527 | 8/1992 | Miller et al. | 604/411 |
| 5,255,676 | 10/1993 | Russo | 604/905 |
| 5,303,751 | 4/1994 | Slater et al. | 604/408 |

FOREIGN PATENT DOCUMENTS

| | | |
|---|---|---|
| 0 476 386 A1 | 3/1992 | European Pat. Off. . |
| 43 18 101 A1 | 12/1994 | Germany . |

*Primary Examiner*—Debra S. Brittingham
*Assistant Examiner*—Ki Yong O
*Attorney, Agent, or Firm*—Hill, Steadman & Simpson

[57] ABSTRACT

An assembly having a puncturing device and a receiving device is provided. The puncturing device has a puncturing element and a blocking element. The puncturing element is joined to a flexible tube and provided with a needle-shaped part. The needle-shaped part has a portion whose cross-section has at least one part set back in relation to a circle circumscribing the cross-section. The receiving device is joined to a sealed container and has a central longitudinal channel which is intended to receive, in a leak-proof manner, the needle-shaped part of the puncturing device. The channel has a portion with a cross-section complementing the portion of the needle-shaped part and a portion intended to cooperate with the blocking element of the puncturing device to form, when the puncturing device is situated in the final position in the receiving device, a leak-proof connection bringing the inside of the container into communication with the feed tube.

9 Claims, 4 Drawing Sheets

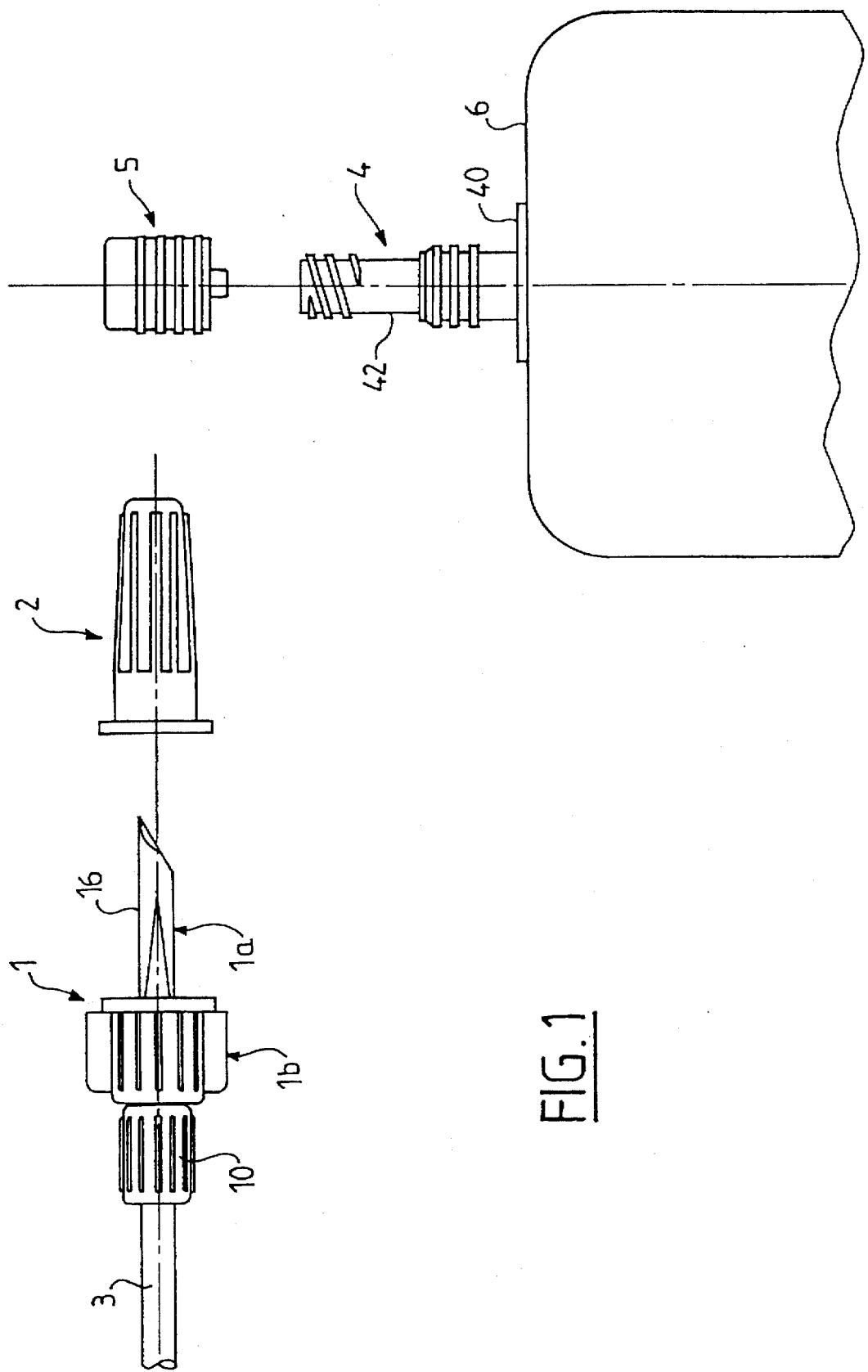

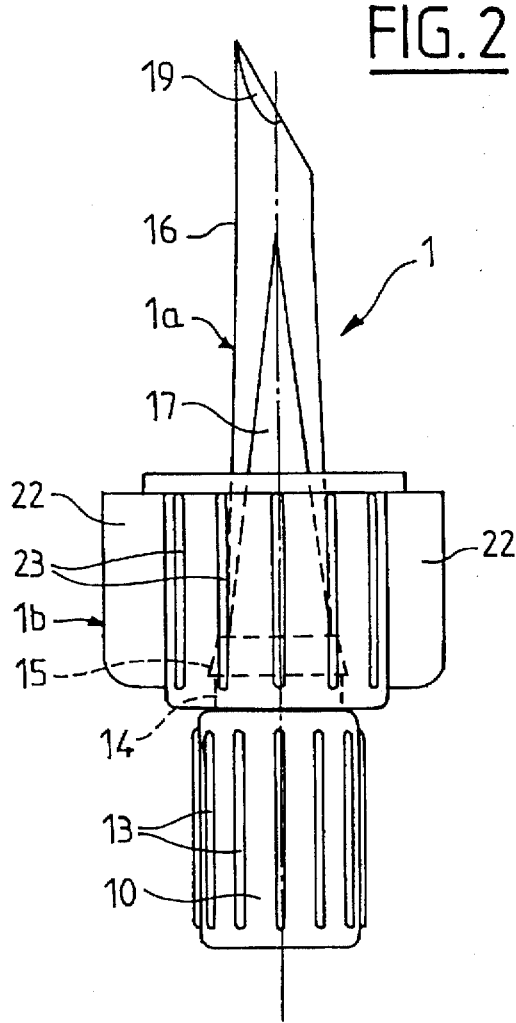
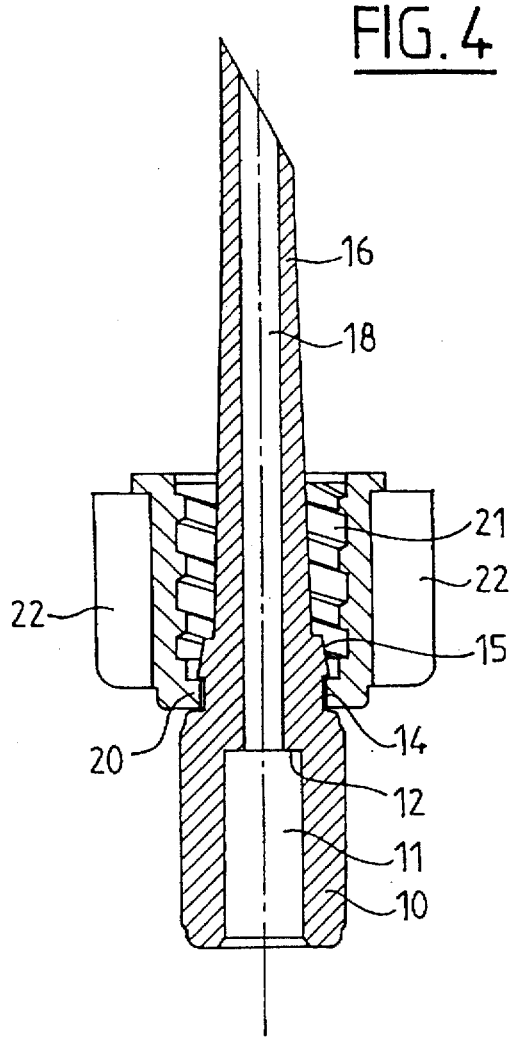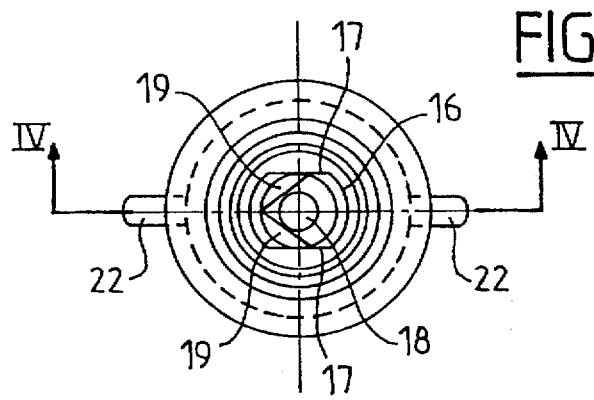

NON-SPIKABLE CONNECTOR

BACKGROUND OF THE INVENTION

The present invention relates in a general manner to enteral feeding systems, and more particularly to a connection assembly which is intended to bring the inside of a sealed container into communication with a feed tube for feeding a patient by the enteral route.

Following an operation, or more generally when a person is no longer able to take food naturally, it is often necessary to provide this person with the necessary foods directly by the enteral route. In the enteral feeding systems, the foods, in the form of a nutrient liquid, are contained in a sealed flask which is generally rigid and which, at the moment of use, has to be connected to and brought into communication with an enteral feed tube.

It must be possible for such a connection to be made under aseptic conditions, preventing any contamination of the nutrient liquid contained in the flask, and the connection must be reliable, that is to say it must neither leak nor become blocked during use. In addition, these enteral feeding systems are generally used in a medical environment in which other systems for treating the patient are found, such as, in particular, parenteral or intravenous injection systems, and it is important that when the enteral feeding system is put in place, the operator cannot inadvertently connect the flask containing the nutrient liquid to a system for intravenous injection.

Furthermore, the containers hitherto used for the nutrient liquid have been rigid flasks sealed by means of a cap which the operator pierces before connecting the flask to the feed tube. Such a procedure, in which the flask is opened prior to the connection, involves a risk of contamination of the nutrient liquid, a risk which it would be desirable to avoid. It would also be desirable to be able to use flexible bags, instead of rigid flasks, for containing the nutrient liquid, these flexible bags being similar to those used for storing blood products used for transfusions.

SUMMARY OF THE INVENTION

The present invention thus relates to a puncturing device, in particular for an enteral feeding system, which remedies the above drawbacks.

The present invention also relates to a connection assembly for an enteral feeding system which remedies the above drawbacks.

More particularly, the present invention relates to a connection assembly which makes it possible to use, as the container, either a sealed rigid flask or a sealed flexible bag.

In addition, the invention relates to such a connection assembly which ensures that the container containing the nutrient liquid is brought into communication with the enteral feed tube under optimum aseptic conditions.

The invention further relates to such a connection assembly which, when a sealed flexible bag is used as the container, prevents any risk of the enteral feeding system becoming blocked by the flexible material of the bag.

The invention also relates to a connection assembly which prevents any error on the part of the operator, and in particular which prevents any possibility of connection to an intravenous injection system.

According to the present invention, the above aims are achieved by providing a puncturing device having a central longitudinal channel extending from one end to the other and having a tubular base and a tubular spiking element which terminates in a free end. The central longitudinal channel defines an open recess in one end of the tubular base for receiving and holding one end of the feed tube and has an opening at the free end of the tubular spiking element for receiving fluid from the sealed container. The tubular spiking element has a substantially circular cross-section and increases in outer diameter from its free end to a position adjacent the tubular base. The tubular spiking element has a planar cut back in its outer surface extending longitudinally from a position adjacent the tubular base to a position intermediate the tubular base and the free end of the tubular spiking element. A tubular receiving device is connected to the sealed container and has a central longitudinal channel leading to the sealed container. The central longitudinal channel is complementary to the tubular spiking element of the puncturing device for receiving the tubular spiking element and provides a leak-proof connection.

The invention also relates to a connection device having a puncturing device as described above and a receiving device having a tubular element having a central longitudinal channel in communication with the interior of a sealed container that is capable of receiving the puncturing device to form a leak-proof connection.

More precisely, the above claims are achieved by inventively providing a connection assembly for fluid connection between a sealed container and an enteral feed tube. The assembly has, in combination, a puncturing device having a central longitudinal channel extending from one end to the other and having a tubular base and a tubular spiking element which terminates in a free end. The central longitudinal channel defines an open recess in one end of the tubular base for receiving and holding one end of the feed tube and has an opening at the free end of the tubular spiking element for receiving fluid from the sealed container. The tubular spiking element has a substantially circular cross-section and increases in outer diameter from its free end to a position adjacent the tubular base. The tubular spiking element has a planar cut back in its outer surface extending longitudinally from a position adjacent the tubular base to a position intermediate the tubular base and the free end of the tubular spiking element. A blocking element is positioned on the puncturing device. A tubular receiving device has a base connected to the sealed container and a tubular element projecting from the base. The tubular element has a central longitudinal channel extending from an orifice in the base to a free end of the tubular element to provide an opening. The central longitudinal channel is complementary to the tubular spiking element of the puncturing device for receiving the tubular spiking element. A locking means on the tubular element adjacent its free end is complementary to the blocking element for releasably locking the puncturing device to the tubular receiving element and providing a leak-proof connection.

In a preferred embodiment of the invention, the complementary portions of the needle-shaped part and of the tubular element have a cross-section of a general oval shape.

In the context of the present invention, the term "substantially circular cross-section" is to be understood as referring to a cross-section of a general circular or oval shape.

In a more particularly preferred embodiment, these complementary portions have at least one flat part or, better still, two diametrically opposite flat parts. Thus, as these complementary portions match each other closely to form a leak-proof connection, on account of the oval shape or of the presence of the flat part or parts, only the specially designed puncturing device of the enteral feeding system can be introduced into the complementary receiving device, forming a leak-proof connection.

To increase further the degree of safety and to limit as far as possible the risk of an incorrect connection being made by the user, the puncturing and receiving devices of the connection assembly can be given a particular color, for example green, clearly distinguishing the connection assembly from other assemblies, such as those for intravenous injections.

In order to avoid any risk of contamination of the nutrient liquid contained in, for example, a flexible bag when the flexible bag is pierced to bring it into communication with the feed tube, the blocking element of the puncturing device and the complementary means of the receiving device are designed in such a way that, during the initial introduction by sliding the needle-shaped part of the puncturing element into the central longitudinal channel of the tubular element of the receiving device, this needle-shaped part is contained entirely within the receiving device. When the blocking element of the puncturing device and the cooperating means on the tubular element of the receiving device are subsequently engaged with one another, the needle-shaped part moves forward in the longitudinal channel of the tubular element of the receiving device in order to project through the central orifice of the base of the tubular element of the receiving device until a final blocking position is reached, in which the needle-shaped part has punctured the wall of the container, for example a bag containing the nutrient liquid, to bring the inside of the container into communication with the enteral feed tube.

In a preferred embodiment, the blocking element is formed by a ring equipped with an internal thread and held on the puncturing element by means of an annular transverse end rim which is engaged in a circular groove formed in the needle-shaped part of the puncturing element near the tubular base of the latter, while the cooperating means of the tubular element of the receiving device is in this case formed by an external thread near the free end of the tubular element of the receiving device. The threaded ring turns freely in the groove of the needle-shaped part of the puncturing element in such a way that when this ring is screwed onto the complementary thread exhibited by the tubular element, it exerts a force on the front rim of the groove, causing the puncturing element to move forward in the tubular element of the receiving device until it reaches the final blocking position. In this final blocking position, the needle-shaped part of the puncturing element projects from the central orifice of the base of the receiving device to pierce a wall of the container. Thus, the container, for example a sealed flexible bag, is pierced and brought into communication with the feed tube only when the connection assembly has been put in place and is protecting the inside of the container from possible contamination.

In a preferred embodiment, the puncturing device and the receiving device are made of a plastic material, for example by injection molding. It is particularly recommended that the plastic material for the puncturing device be an ABS resin which can be solution-dyed, for example green, and that the plastic material for the receiving device be polyethylene, which can likewise be solution-dyed, for example green. The puncturing element of the puncturing device is preferably injection-molded in one piece, whereas the blocking element is injection-molded separately and then fitted by force onto the puncturing element. In general, the receiving device is also injection-molded in one piece.

In order to avoid any contamination prior to the connection, a cap is provided which is generally made of plastic material (for example polyethylene) and which fits on the needle-shaped part of the puncturing element of the puncturing device. Of course, a stopper is also provided which is made, for example, by injection of polyethylene and which fits in a leak-proof manner on the free end of the receiving device fixed to the container, for example a sealed flexible bag.

These and other advantages of the present invention are described in, and will be apparent from, the detailed description of the presently preferred embodiments and from the drawings.

BRIEF DESCRIPTION OF THE DRAWINGS

FIGS. 1A and 1B show exploded views of an embodiment, according to the invention, of a connection assembly for an enteral feeding system.

FIG. 2 shows a side view of an embodiment of a puncturing device in a connection assembly according to the present invention.

FIG. 3 shows a plan view of the puncturing device in FIG. 2.

FIG. 4 shows a cutaway view along the line IV—IV in FIG. 2.

DETAILED DESCRIPTION OF THE PRESENTLY PREFERRED EMBODIMENTS

Figure 5:
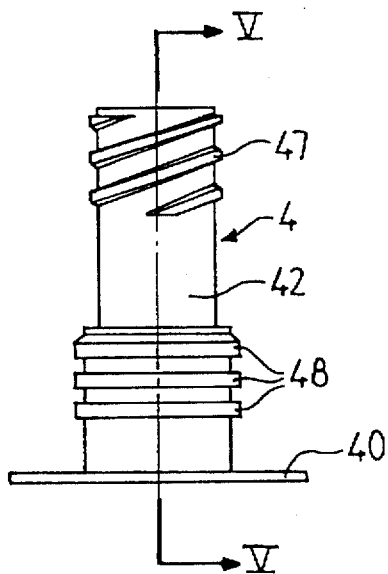
FIG. 5 shows a side view of an embodiment of a receiving device in the connection assembly according to the invention.

Referring to FIGS. 1A and 1B, exploded views of a connection assembly for an enteral feeding system according to the invention are shown.

In a general manner, the connection assembly has a puncturing device 1 and a receiving device 4. More particularly, the puncturing device 1 has a puncturing element 1a which is connected to a feed tube 3, and a blocking nut 1b which is held rotationally on the puncturing element 1a. As can be seen in FIG. 1A, during storage of the puncturing device 1, a cap 2 is placed on the puncturing element 1a in order to protect this element from any contamination.

The receiving device 4 has a base 40 and a tubular element 42 projecting from the base 40. As is shown in FIG. 1B, the receiving device 4 is fixed by any suitable means, for example by adhesive bonding or heat sealing of the base 40 to a sealed container, for example a flexible bag of plastic material 6, containing a nutrient liquid. In the same way as for the puncturing device 1, a stopper 5 is provided, for example a hollow cylindrical stopper equipped with a central stud which fits on the free end of the receiving device 4 to close the opening thereof, in order to prevent any contamination of the receiving device 4 during storage and before use. The puncturing device 1 and the receiving device 4 of the connection assembly are preferably formed by injection-molding of plastic material, for example an ABS resin and polyethylene, respectively.

The puncturing device 1 and the receiving device 4 of the connection assembly according to the invention will now be described in detail in conjunction with FIGS. 2 to 4 and FIGS. 5 to 8, respectively.

Referring particularly to FIGS. 2 to 4, a puncturing device 1 of a connection assembly according to the invention has been shown. As can be seen in the figures, the puncturing device 1 has a puncturing element 1a made in one piece and having a base 10 of general cylindrical shape joined to a needle-shaped part 16. The cylindrical base 10 has a central recess 11 of general cylindrical shape which terminates, at its rear or free end, in a bevelled opening. The outer lateral surface of the base 10 is preferably provided with longitudinal ribs 13 which reinforce the base 10 and permit better gripping thereof. The recess 11 of the base 10 communicates, at its front end, with a central longitudinal channel 18 of general cylindrical shape formed in the needle-shaped part 16. The central longitudinal channel 18 of the needle-shaped part 16, which is coaxial with the recess 11, has a diameter smaller than the recess 11, thereby forming an annular support surface 12. One end of a flexible tube 3, having an external diameter approximately equal to the internal diameter of the recess 11, is introduced into this recess until its annular end edge is supported against the annular support surface 12. The introduced end of the flexible tube 3 can be fixed in a permanent manner to the cylindrical base 10 by any suitable means, for example by adhesive bonding or heat sealing. The inner channel of the flexible tube 3 is preferably of a diameter generally equal to the diameter of the central longitudinal channel 18 of the needle-shaped part 16 and is aligned with this channel. The central longitudinal channel 18, of general cylindrical shape, of the needle-shaped part 16 opens out at the front or free end of the needle-shaped part 16, thus bringing the cylindrical recess 11 of the base 10 into communication with the outside. As can be seen in FIGS. 2 and 4, the front or free end of the needle-shaped part 16 is bevelled in such a way that the central longitudinal channel 18 terminates, at this free end, in an orifice of oval shape. Moreover, the free end of the needle-shaped part 16 is provided with two symmetrical lateral recesses 19, conferring a tapered, pointed shape to the free end of the needle-shaped part 16 for easier piercing of the wall of the container.

According to the invention, a portion of the needle-shaped part 16 is provided with two diametrically opposite flat parts 17 which extend from an annular projection 15 which is formed on the needle-shaped part 16, in proximity to the base 10, and which will be described in more detail hereinbelow. The flat parts 17 have a length equal to approximately three quarters of the total length of the needle-shaped part 16. These two diametrically opposite flat parts 17 form, in the needle-shaped part 16, a portion of generally oval shape or, more generally, a portion of the needle-shaped part 16 having a cross-section provided with a part set back in relation to a circle circumscribing this cross-section. The length as well as the shape of these flat parts 17 are not critical as long as they form, on the needle-shaped part 16, a portion whose cross-section has at least one part set back in relation to the circle circumscribing this cross-section. Similarly, the number of flat parts 17 is not critical, and it is possible to arrange only one of them or more than two of them, as appropriate. The function of these flat parts 17 will be described hereinafter in conjunction with the description of the connection of the puncturing device 1 to the receiving device 4.

As indicated above, the needle-shaped part 16 has an annular projection 15 which is spaced slightly apart from the front transverse surface of the cylindrical base 10, the annular projection 15 and the front transverse wall of the cylindrical base 10 thereby defining between them an annular groove 14.

In a preferred embodiment, the cylindrical base 10 and the needle-shaped part 16 are molded in one piece, for example by injection-molding of an ABS resin.

As can be seen particularly in FIGS. 2 and 4, the puncturing device 1 additionally comprises a blocking nut 1b. This blocking nut 1b has the general form of an annular ring provided at its rear end with an annular transverse rim 20 delimiting a cylindrical central opening which is of a diameter slightly greater than the diameter of the groove 14 formed in the needle-shaped part 16, but smaller than the diameter of the annular projection 15, so that, by means of force-fitting, the annular rim 20 comes to sit in this groove 14 and is held therein, while at the same time being able to turn about the central axis of the puncturing device 1. As can be seen better in FIG. 4, the nut 1b is equipped with an internal thread 21. It is also possible to provide two diametrically opposite ribs or lugs 22 on the outer lateral wall of the nut 1b to permit easier gripping and turning of the nut 1b. It is also possible, preferably, to provide longitudinal ribs 23 of low height on the outer lateral surface of the nut 1b to reinforce the latter and to render its manipulation easier. The function of the blocking nut 1b will be described more completely during the description of the connection of the puncturing device 1 to the receiving device 4. In general, this nut 1b is made in one piece by molding, for example by injection-molding of an ABS resin.

Figure 6:
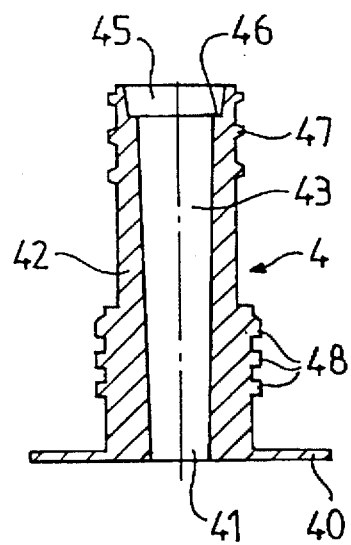
FIG. 6 shows a cutaway view of the receiving device along the line VI—VI in FIG. 5.
Figure 7:
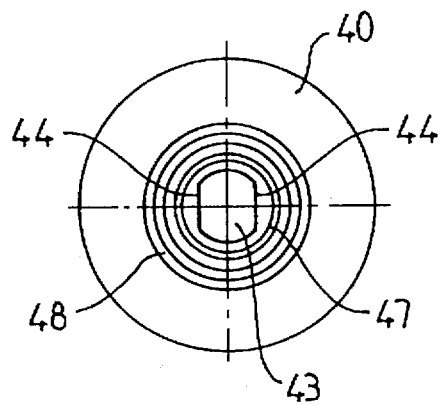
FIG. 7 shows a plan view of the receiving device in FIG. 5.
Figure 8:
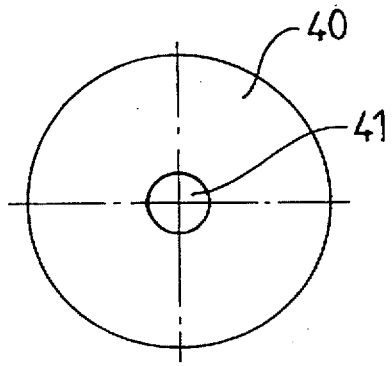
FIG. 8 shows a bottom view of the receiving device in FIG. 5.
Figure 9:
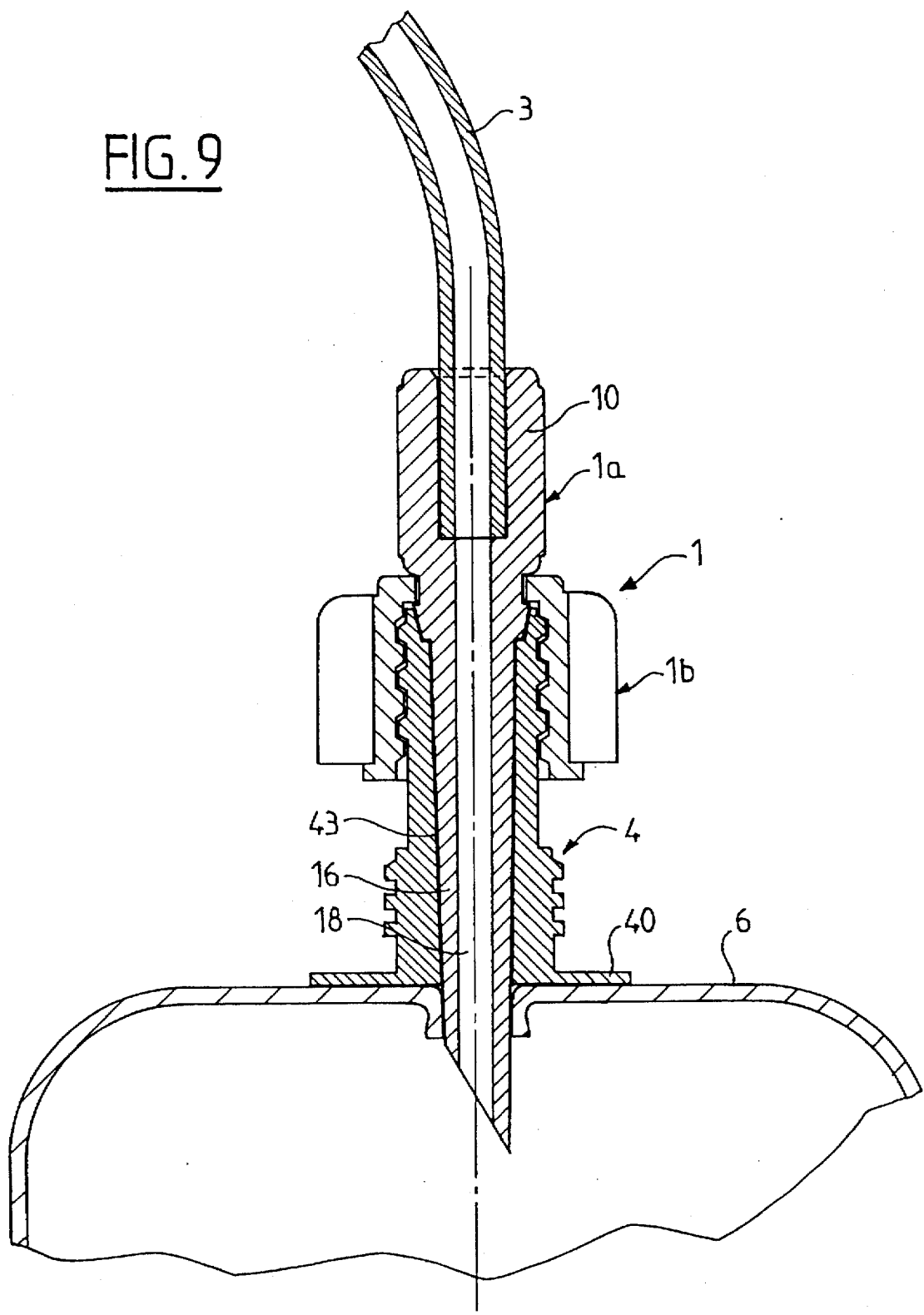
FIG. 9 shows a cutaway view of the puncturing and receiving devices in FIGS. 2 and 5, once they have been assembled.

Referring now to FIGS. 5 to 8, a receiving device 4 in an embodiment of a connection assembly according to the invention has been shown. As can be seen in the figures, the connection device 4 has a base 40 presented in the form of a disc which is provided with a central circular opening 41 and which is intended to be connected to a sealed container, for example a sealed flexible bag, by any suitable means such as adhesive bonding or heat sealing. The receiving device 4 additionally has a tubular element 42 projecting from the base 40 and generally formed integrally therewith. The tubular element 42 has a longitudinal central channel 43 which communicates with the central opening 41 of the base 40 and which terminates, at the front or free end of the tubular element 42, in an open recess 45. The central longitudinal channel 43 of the receiving device 4 has a size and shape such that it can receive the needle-shaped part 16 of the puncturing device 1 in a leak-proof manner. In particular, in the embodiment represented, the central longitudinal channel 43 of the receiving device 4 has two diametrically opposite flat parts 44 which extend from the recess 45 over a distance equal to approximately three quarters of the total length of the tubular element 42 of the receiving device 4. The tubular element 42 of the receiving device 4 additionally has on its outer lateral surface, near its front free end, a thread 47 complementing the internal thread of the nut 1b of the puncturing device 1. Finally, it is also possible to provide, in a preferred manner, one or more annular ribs (for example three ribs as shown in FIGS. 5 and 6) on the outer lateral surface of the tubular element 42, in proximity to the base 40 of the receiving device 4. These ribs increase the rigidity of the tubular element 42.

The receiving device 4 is preferably molded in one piece, for example by injection molding of polyethylene.

The connection of the puncturing device 1 and of the receiving device 4 of the connection assembly according to the invention will now be described with reference to FIGS. 1A, 1B and 2–9.

Once the puncturing device 1 has been connected to the flexible tube 3, and the receiving device 4 has been joined to a container, for example a sealed bag 6 containing a nutrient liquid, the protective cap 2 for the needle-shaped part 16 of the puncturing device 1 is removed, and the protective stopper 5 for the receiving device 4 is removed. The operator then inserts the needle-shaped part 16 of the puncturing device 1 into the central longitudinal channel 43 of the tubular element 42 of the receiving device 4. Due to the presence of the flat parts 17 on the needle-shaped part 16 of the puncturing device 1 and to the presence of the corresponding flat parts 44 in the central longitudinal channel 43 of the tubular element 42 of the receiving device 4, the operator can insert into this receiving device 4 only the appropriate puncturing device 1 and could not introduce, for example, a needle of similar diameter having a circular cross-section. Thus, the operator cannot make the mistake of introducing a connection needle of an intravenous injection system into the receiving device 4 according to the invention.

On account of the presence of the thread 46 on the outer lateral wall of the tubular element 42 of the receiving device 4, in proximity to the free or front end of the tubular element 42, the needle-shaped part 16 can at first only be slid into the longitudinal channel 43 of the tubular element 42 by a distance which is such that it is contained entirely within the receiving element and cannot project from the latter through the central orifice 41 of the base 40 of the receiving element, since the internal thread 21 of the nut 1b comes into abutment against the external thread 47 of the tubular element 42 of the receiving device 4, preventing the operator from continuing the sliding introduction of the puncturing device 1. The operator must then turn the nut 1b in order to screw it onto the thread 47 of the tubular element 42 of the receiving device 4. By screwing the nut 1b in this way, the operator drives the puncturing element 1a in translation on account of the force exerted by the annular rim 20 of the nut 1b on the annular projection 15 of the needle-shaped part 16, until this annular projection 15 comes into abutment against an annular support surface formed at the interface between the annular recess 45, at the free end of the tubular element 42, and the central longitudinal channel 43 of the tubular element 42 of the receiving device 4. During the screwing, the advance of the puncturing element 1a causes the bevelled end of the needle-shaped part 16 to project out from the circular opening 41 of the base 40 of the receiving element 4. The needle-shaped part 16 punctures the sealed wall of the bag 6 to bring the inside of the bag 6 into communication with the inner channel of the flexible tube 3 by way of the central longitudinal channel 18 of the needle-shaped part 16 communicating with the inner channel of the tube 3 inserted in the recess 11 of the cylindrical base 10 of the puncturing element 1a. Thus, the puncturing of the sealed bag 6 is effected only when the nut 1b has been screwed, at least in part, onto the external thread 47 of the tubular element 42 of the receiving device 4, thereby avoiding any risk of contamination of the contents of the bag 6.

According to the invention, a connection system for enteral feeding has thus been formed which is safe and leak-proof and which permits the use of a flexible container and avoids any risk of the container being linked up to a system other than the enteral feeding system.

We claim:

1. A connection assembly for providing fluid connection between a sealed container and an enteral feed tube, the assembly comprising, in combination:

a puncturing device having a central longitudinal channel extending from one end to the other and having a tubular base and a tubular spiking element which terminates in a free end, the central longitudinal channel defining an open recess in one end of the tubular base for receiving and holding one end of the feed tube and having an opening at the free end of the tubular spiking element for receiving fluid from the sealed container, the tubular spiking element being of a substantially circular cross-section and increasing in outer diameter from its free end to a position adjacent the tubular base, and the tubular spiking element having a planar cut back in its outer surface extending longitudinally from a position adjacent the tubular base to a position intermediate the tubular base and the free end of the tubular spiking element;

a blocking element positioned on the puncturing device; and a tubular receiving device having a base connected to the sealed container and a tubular element projecting from the base, the tubular element having a central longitudinal channel extending from an orifice in the base to a free end of the tubular element to provide an opening, the central longitudinal channel being complementary to the tubular spiking element of the puncturing device for receiving the tubular spiking element, and a locking means on the tubular element adjacent its free end that is complementary to the blocking element for releasably locking the puncturing device to the tubular receiving element and providing a leak-proof connection.

2. The assembly of claim 1 in which the tubular spiking element has a pair of planar cut backs in its outer surface, each cut back extending longitudinally from a position adjacent the tubular base to a position intermediate the tubular base and the free end of the tubular spiking element.

3. The assembly of claim 2 in which the cut backs are positioned diametrically opposite each other.

4. The assembly of claim 1 in which the blocking element is a nut which is rotatably fitted on the puncturing device, the nut having an internal thread.

5. The assembly of claim 2 in which the puncturing device has a circumferential groove between the tubular base and the tubular spiking element, and the nut has a complementary rib which engages in the groove for rotatably holding the nut on the puncturing device.

6. The assembly of claim 4 in which the locking means on the tubular element is an external thread complementary to the internal thread of the nut.

7. The assembly of claim 5 in which the locking means on the tubular element is an external thread complementary to the internal thread of the nut.

8. The assembly of claim 1 in which the tubular spiking element of the puncturing device pierces beyond the orifice of the base of the tubular receiving device and into the sealed container only when the locking element and locking means are engaged.

9. The assembly of claim 1 in which the puncturing element is made in one piece of ABS resin, the blocking element is made in one piece of ABS resin, and the receiving device is made in one piece from polyethylene.

* * * * *